US011406255B2

(12) United States Patent
Swisher

(10) Patent No.: US 11,406,255 B2
(45) Date of Patent: Aug. 9, 2022

(54) SYSTEM AND METHOD FOR DETECTING ABNORMAL TISSUE USING VASCULAR FEATURES

(71) Applicant: KONINKLIJKE PHILIPS N.V., Eindhoven (NL)

(72) Inventor: Christine Menking Swisher, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 211 days.

(21) Appl. No.: 16/959,772

(22) PCT Filed: Jan. 3, 2019

(86) PCT No.: PCT/EP2019/050117
§ 371 (c)(1),
(2) Date: Jul. 2, 2020

(87) PCT Pub. No.: WO2019/134945
PCT Pub. Date: Jul. 11, 2019

(65) Prior Publication Data
US 2020/0359884 A1    Nov. 19, 2020

Related U.S. Application Data

(60) Provisional application No. 62/613,080, filed on Jan. 3, 2018.

(51) Int. Cl.
*G06K 9/00* (2022.01)
*A61B 1/313* (2006.01)
(Continued)

(52) U.S. Cl.
CPC ........ *A61B 1/3137* (2013.01); *A61B 1/00009* (2013.01); *A61B 1/00045* (2013.01);
(Continued)

(58) Field of Classification Search
CPC .............. A61B 1/3137; A61B 1/00009; A61B 1/00045; G02B 27/017; G06F 3/011;
(Continued)

(56) References Cited

U.S. PATENT DOCUMENTS 6,139,490 A   10/2000  Breidenthal
7,121,781 B2  10/2006  Sanchez
(Continued)

OTHER PUBLICATIONS

PCT International Search Report, International application No. PCT/EP2018/086871, dated Mar. 28, 2019.
(Continued)

*Primary Examiner* — Tom Y Lu
(74) *Attorney, Agent, or Firm* — Sherry Austin

(57) ABSTRACT

A imaging system includes a camera, a display and a processor. The camera has color video acquisition capability, and is mounted to a distal end of an interventional instrument insertable within an object, the camera providing image frames for imaging vasculature of the object, each image frame including multiple pixels providing corresponding signals, respectively. The processor is programmed to receive the signals; amplify variations in at least one of color and motion of the signals corresponding to the multiple pixels; determine spatial phase variability, frequency and signal characteristics of at least some of the amplified signals corresponding to the multiple pixels, respectively; identify pixels indicative of abnormal vascularity based on the spatial phase variability, frequency and/or signal characteristics; create a vascular map corresponding to each, where each vascularity map includes a portion of the object having the abnormal vascularity; and operate the display to display each vascularity map.

15 Claims, 8 Drawing Sheets

(51) Int. Cl.
*A61B 1/00* (2006.01)
*G02B 27/01* (2006.01)
*G06F 3/01* (2006.01)
*G06T 7/00* (2017.01)

(52) U.S. Cl.
CPC ............ *G02B 27/017* (2013.01); *G06F 3/011* (2013.01); *G06T 7/0012* (2013.01); *G06T 2207/10016* (2013.01); *G06T 2207/10024* (2013.01); *G06T 2207/10068* (2013.01); *G06T 2207/20056* (2013.01); *G06T 2207/30101* (2013.01)

(58) Field of Classification Search
CPC ......... G06T 7/0012; G06T 2207/10016; G06T 2207/10024; G06T 2207/10068; G06T 2207/20056; G06T 2207/30101; G06T 2207/10072
See application file for complete search history.

(56) References Cited

U.S. PATENT DOCUMENTS

| | | | |
|---|---|---|---|
| 9,095,252 B2 | 8/2015 | Popovic | |
| 10,986,987 B2* | 4/2021 | Aoyama | .................. A61B 1/06 |
| 11,103,200 B2* | 8/2021 | Kohli | ..................... A61B 6/461 |
| 11,185,214 B2* | 11/2021 | Yamamoto | ....... A61B 1/000094 |
| 2004/0236225 A1 | 11/2004 | Murphy | |
| 2007/0287897 A1 | 12/2007 | Faris | |
| 2014/0036054 A1 | 2/2014 | Zouridakis | |
| 2014/0046197 A1 | 2/2014 | Lucassen | |
| 2017/0294015 A1 | 10/2017 | Wang | |
| 2018/0214009 A1* | 8/2018 | Endo | .................... A61B 1/3137 |
| 2018/0276823 A1* | 9/2018 | Barral | .................. A61B 5/7425 |

OTHER PUBLICATIONS

McLeod J. et al., "Exploiting Temporal Image Information in Minimally Invasive Surgery", Electronic Thesis and Dissertation Repository. 5167, Jan. 1, 2017 (Jan. 1, 2017), pp. 1-179, XP055580137.
Alborz Amir-Khali Li Ei Al., "Automatic Segmentation of Occluded Vasculature Via Pulsatile Motion Analysis in Endoscopic Robot-Assisted Partial Nephrectomy Video", Medical Image Analysis, vol. 25, No. 1, Oct. 1, 2015 (Oct. 1, 2015), pp. 103-110, XP55475378,.
Nu et al., "Eulerian Video Magnification for Revealing Subtle Changes in the World," ACM Transactions on Graphics vol. 31 No. 4, (Proc. SIGGRAPH, 2012).

\* cited by examiner

SYSTEM AND METHOD FOR DETECTING ABNORMAL TISSUE USING VASCULAR FEATURES

CROSS-REFERENCE TO RELATED APPLICATIONS

This patent application claims the priority benefit under 35 U.S.C. § 371 of International Patent Application no. PCT/EP2019/050117 filed Jan. 3, 2019, which claims the benefit of U.S. Application Ser. No. 62/613,080, filed on Jan. 3, 2018. These applications are hereby incorporated by reference herein in their entirety.

BACKGROUND

Detection of tumors using vascularization is currently used in medical imaging. That is, tumors may be detected by analysis of the blood vessels within the tumors because, as compared to normal blood vessels, these tumor blood vessels are generally dilated with irregular shapes, disorganized connections, and leaky capillaries. For example, dynamic imaging of contrast agents injected into a venous system may be used to detect areas of increased vascularity, angiogenesis and vessel leakiness, all of which are indicative of cancerous tumors. However, cameras and optic imagers have not been used for cancerous tumor detection, even though video assisted surgery is becoming more common. Minimally invasive surgery often results in improved patient outcomes.

Differentiation of normal from abnormal tissue intraoperatively is often a challenge for surgeons. Such differentiation may be particularly difficult for non-palpable/non-tactile tumors often seen in brain cancer (e.g., neurosurgery), lung cancer (e.g., ground glass opacities on computerized tomography (CT) scans), liver cancer (e.g., diffuse liver disease), and other cancers in soft tissues. Also, during robotic surgery, the surgeon cannot use tactile features to differentiate tumors. Difficulties also may arise when surgical planning information acquired from CT scans, magnetic resonance imaging (MRI) scans and/or positron emission tomography (PET) scans fail to assist in determining tumor (or lesion) location due to tissue deformation. This often arises during thoracic surgery due to pneumothorax, and during neurosurgery due to cerebrospinal fluid (CSF) loss, for example.

Also, use of surgical robots and/or steerable devices for visually assisted, minimally invasive surgery limits direct visual access potentially abnormal tissue. Examples of surgical robots include multi-arm systems, such as da Vinci® robots, or flexible robots, such as Medrobotics Flex® robotic systems. These robotic systems are controlled by the surgeon (or user) using different interface mechanisms, including hand controllers, input handles and/or heads-up display (HUD) devices (e.g., head-mounted display (HMD) devices) for the operating robotic systems, and image displays for capturing endoscope video and displaying various control modes of the robotic systems.

Accordingly, it is desirable to be able to accurately detect tumors using images of vascularization obtained from cameras insertable within a body, during surgery or other interventional procedures.

SUMMARY

According to an illustrative embodiment, a imaging system includes a camera, a display and a processor. The camera has color video acquisition capability, and is mounted to a distal end of an interventional instrument insertable within an object. The camera provides image frames for imaging vasculature of the object, each image frame including multiple pixels providing corresponding signals, respectively. The processor is programmed to receive the signals; amplify variations in at least one of color and motion of the signals corresponding to the multiple pixels to provide amplified signals; determine at least one of spatial phase variability, frequency and signal characteristics of at least some of the amplified signals corresponding to the multiple pixels, respectively; identify pixels of the multiple pixels indicative of abnormal vascularity based on the at least one of spatial phase variability, frequency and signal characteristics of the at least some of the amplified signals; create a vascular map corresponding to each of the at least one of spatial phase variability, frequency and signal characteristics of the at least some of the amplified signals using the identified pixels, each vascularity map including a portion of the object having the abnormal vascularity; and operate the display to display each vascularity map.

According to another illustrative embodiment, a method is provided for identifying abnormal vascularity, indicating abnormal tissue within a subject, using images from a camera having color video acquisition capability and mounted to a distal end of an interventional instrument insertable within the subject. The method includes receiving signals corresponding to multiple pixels in each of multiple image frames provided by the camera of a target portion in the subject for imaging vasculature of the target portion; amplifying variations in at least one of color and motion of the signals corresponding to the multiple pixels in each of the multiple image frames to provide amplified signals, respectively; determining at least one of spatial phase variability, frequency and signal characteristics of at least some of the amplified signals corresponding to the multiple pixels, respectively; identifying pixels of the plurality of pixels in each of the plurality of image frames indicative of abnormal vascularity based on the at least one of spatial phase variability, frequency and signal characteristics of the at least some of the amplified signals; creating a vascular map corresponding to each of the at least one of spatial phase variability, frequency and signal characteristics of the at least some of the amplified signals using the identified pixels, each vascularity map including a portion of the subject having the abnormal vascularity; and displaying each vascularity map. The method may further include combining at least two of the vascular maps corresponding to each of the at least one of spatial phase variability, frequency and signal characteristics of the at least some of the amplified signals to create an aggregate vascular map; and displaying the aggregate vascular map.

According to another illustrative embodiment, a computer readable medium is provided containing software, executable by a computer processor, for identifying abnormal vascularity, indicating abnormal tissue within a subject, using images from a camera having color video acquisition capability and mounted to a distal end of an interventional instrument insertable within the subject. The computer readable medium includes receiving code for receiving signals corresponding to multiple pixels in each of multiple image frames provided by the camera via the interventional instrument of a target portion in the subject for imaging vasculature of the target portion; amplifying code for amplifying variations in at least motion of the signals corresponding to the multiple pixels in each of the multiple image frames to provide amplified signals, respectively; determining code for determining at least one of spatial phase variability, frequency and signal characteristics of at least some of the amplified signals corresponding to the multiple pixels, respectively; identifying code for identifying pixels of the multiple pixels in each of the multiple image frames indicative of abnormal vascularity based on the at least one of spatial phase variability, frequency and signal characteristics of the at least some of the amplified signals; creating code for creating a vascular map corresponding to each of the at least one of spatial phase variability, frequency and signal characteristics of the at least some of the amplified signals using the identified pixels, each vascularity map including a portion of the subject having the abnormal vascularity; combining code for providing an aggregate vascular map by combining at least two of the vascular maps corresponding to each of the at least one of spatial phase variability, frequency and signal characteristics of the at least some of the amplified signals; and displaying code for causing the aggregate vascular map to be displayed on a display, the displayed aggregate vascular map indicating the portion of the subject having the abnormal vascularity by enhanced contrast with portions of the subject having normal vascularity.

BRIEF DESCRIPTION OF THE DRAWINGS

The present invention will be more readily understood from the detailed description of exemplary embodiments presented below considered in conjunction with the accompanying drawings, as follows. Like numbered elements in these figures are either equivalent elements or perform the same function. Elements which have been discussed previously will not necessarily be discussed in later figures if the function is equivalent.

DETAILED DESCRIPTION

Embodiments of the present invention will now be described more fully hereinafter with reference to the accompanying drawings, in which embodiments of the present invention are shown. The present invention may, however, be embodied in different forms and should not be construed as limited to the embodiments set forth herein. Rather, these embodiments are provided as teaching examples of the invention.

As mentioned above, intraoperative differentiation of abnormal tissue from normal tissue for excision and biopsy is common challenge for surgeons performing various interventional procedures. According to various embodiments, vascular information extracted after creation of one or more Eulerian video magnification maps indicative abnormal vascularity or hypervasculature may be used to aid surgeons in differentiating the abnormal tissue (e.g., cancerous tumor) from the normal tissue. Additionally, various embodiments may be used for screening suspect melanoma (skin cancer) lesions to improve accuracy and potentially aid in early diagnosis.

Figure 1A:
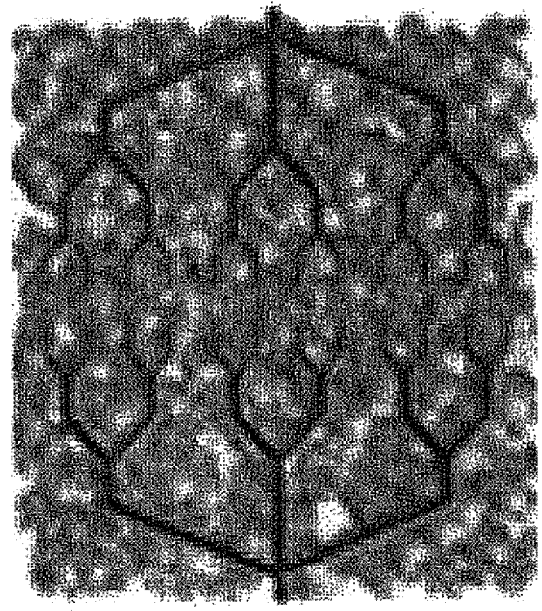
FIG. 1A shows an example of healthy (or normal) tissue with normal vascularity.
Figure 1B:
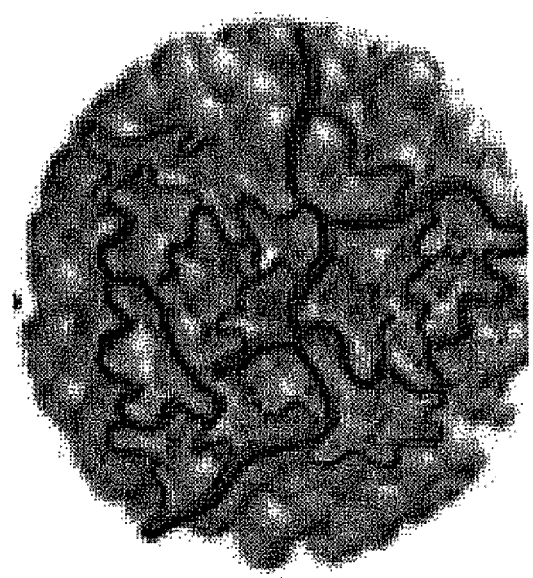
FIG. 1B shows an example unhealthy (or cancerous) tissue with abnormal vascularity, as in a tumor.

Generally, hallmarks of cancer include six biological capabilities acquired during a multistep development of tumors. These hallmarks constitute an organizing principle for rationalizing the complexities of neoplastic disease. Induced angiogenesis is one of the six hallmarks. Angiogenesis enables a tumor comprising cancer cells to have its own blood supply so that it can grow. Unlike normal blood vessels (e.g., blood vessels running through portions of a body unencumbered by cancerous tumors), tumor blood vessels demonstrate various abnormalities, such as being dilated with an irregular shape, having disorganized connections and including leaky capillaries, resulting in irregular blood flow. Such abnormalities may be referred to as hypervascularization. FIGS. 1A and 1B respectively show examples of healthy (or normal) tissue with normal vascularity, and unhealthy or abnormal (e.g., cancerous) tissue with abnormal vascularity, as in a tumor.

According to various embodiments, camera-based detection of pulsatile flow in video is used to detect these and other abnormalities. The camera may be mounted to an interventional instrument or tool, such as an endoscope or catheter, or to a robot arm, to aid in performing interventional procedures on a subject. Throughout the disclosure, "mounted to" means connected to, integrated with and/or contained in. Often, images, including videos, of seemingly static portions of the body actually contain subtle changes that are invisible to the human eye. However, it is possible to measure these subtle changes via the use of algorithms to amplify variations, including for example use of Eulerian video magnification. For example, it is known that a human pulse may be measured from pulse-induced color variations or small motion of pulsatile flow captured by conventional videos, such measurements being referred to as remote photoplethysmography (rPPG). See, e.g., Wu et al., "Eulerian Video Magnification for Revealing Subtle Changes in the World," ACM Transactions on Graphics vol. 31 no. 4 (Proc. SIGGRAPH, 2012).

Generally, a series of images may be taken from a data stream provided by a camera of a vasculature system, where the camera may be mounted to an interventional instrument and the data stream may be already available in the course of performing an interventional procedure. Variations in color and/or motion are amplified in the images indicated by the pixel signals from the camera imaging the vasculature system (e.g., including normal and abnormal tissue). Then, up to three vascular maps may be created and/or combined to differentiate the areas of normal and abnormal tissue. As discussed below, the vascular maps may include, for example, a frequency map, a signal characteristics map and a phase variability map, based on different information from signals corresponding to images of a target portion or ROI.

An aggregate vascular map that combines two or more of the three vascular maps may be generated for enhanced contrast, i.e., better than that of any single vascular map, better differentiating the areas of normal and abnormal tissue. The vascular maps and/or the aggregate vascular map may be displayed with an augmented reality (AU) device, including a heads-up display (HUD), for example, enabling easy visualization, such that the surgeon can remain focused on the surgical field where the abnormal tissue (e.g., tumor) is visually apparent in the vascular maps and/or the aggregate vascular map. One of the vascular maps may be enhanced by training fully convolution neural networks (FCNs) to segment an abnormal area in the target portion or ROI.

The camera-based vascular information also may be used for screening suspect vascular melanoma lesions to improve accuracy and potentially aid in early diagnosis. That is, a camera (externally located, in this instance) may provide images of an apparent lesion, which has a vasculature system. Again, variations in color and/or motion from the pixel signals are amplified, the pixel signals imaging the vasculature system (e.g., including normal and abnormal tissue). Then, the vascular maps may be created and/or combined to differentiate the areas of normal and abnormal tissue in and around the lesion. The vascular information may be combined with other visual cues indicative of malignancy, such as morphology, color, size and temporal change, to further improve accuracy of camera-based screening.

For patients with many lesions, for example, information from color video could aid clinicians in triaging the higher risk lesions for biopsy. Early diagnosis of melanoma is a key determinant of positive prognosis and survival. Also, surgical removal of skin lesions in early stages is typically minimally invasive, while treatment of melanoma in latter stages, e.g., metastatic melanoma, which is aggressive and difficult to treat, results in poorer outcomes. Convolutional neural network (CNNs) trained with data in addition to conventional images may further improve accuracy and potentially aid in early diagnosis of melanoma. Such camera-based vascularity determination can be provided at a subject's home and/or in dermatology clinics, since the determination may be made using the camera, a processor and a memory, as discussed below with reference to FIG. 2. Notably, although the disclosure focuses on imaging and vascularity determination using a camera for interventional procedures, it is understood that the processes for identifying normal and abnormal vasculature, including determination and display of vascular maps and/or an aggregate vascular map, are substantially the same for determining vascularity of a vascular melanoma lesion.

Also, the AR device may be provided for a user (e.g., surgeon) to control a robot through physical movement by the user (e.g., other than use of the user's hands to manipulate conventional manual controls). The user can identify and select a target portion for the robot based on live images received by the AR device from the camera. The live images may be endoscopic images, for example, provided by the camera mounted to the distal end of an endoscopic, e.g., which may be operable by a dedicated endoscope controller, or by a forward-looking camera, e.g., which may be operable by the robot. For example, the AR device may include a heads-up display (HUD) (AR-HUD device) that displays the image(s) on a display in a head piece worn by the user. The AR-HUD device further includes one or more sensors configured to detect motion of the user, such as head motion or eye movement, where the detected motion is processed to select the target portion in the surgical site, shown in the image on the display, for the robot.

Using the live images and the head motion and/or eye movement detection of the user improves usability of the robot by simulating experience during conventional surgery, where the user moves his or her head and/or directs eye movement toward the area (target portion) on which the user is focused, while preserving improved dexterity of a surgical robot. Further, the live images may be used to provide the data stream of the vasculature system, mentioned above. Color and/or motion from these images are magnified to amplify vasculature signals, and to provide the vascular maps depicting the areas of abnormal tissue (e.g., tumors).

It is to be understood that the terminology used herein is for purposes of describing particular embodiments only, and is not intended to be limiting. Any defined terms are in addition to the technical and scientific meanings of the defined terms as commonly understood and accepted in the technical field of the present teachings. Reference in the specification to "one embodiment" or "an embodiment," as well as other variations thereof, means that a particular feature, structure, characteristic, step and so forth described in connection with the embodiment is included in at least one embodiment of the present teachings. Thus, the appearances of the phrase "in one embodiment" or "in an embodiment", as well any other variations, appearing in various places throughout the specification are not necessarily all referring to the same embodiment.

Initially, it is noted that the images may include two-dimensional (2D) or three-dimensional (3D) images, obtained as video or a stream of still images. The 2D or 3D images may be obtained via a camera mounted to a distal end of an endoscope, or via a forward-looking camera provided at the distal end of a robot arm (e.g. as an end effector). Also, the images may be live images captured through the camera during the minimally invasive procedure. In various configurations, the images may be captured by multiple cameras. Other medical imaging may be incorporated during the surgical process, such as images obtained by, X-ray, ultrasound, and/or magnetic resonance, for example, for a broader view of the surgical site and surrounding areas, but may not necessarily be used directly for detection of abnormal vascularity during an interventional procedure.

Figure 2:
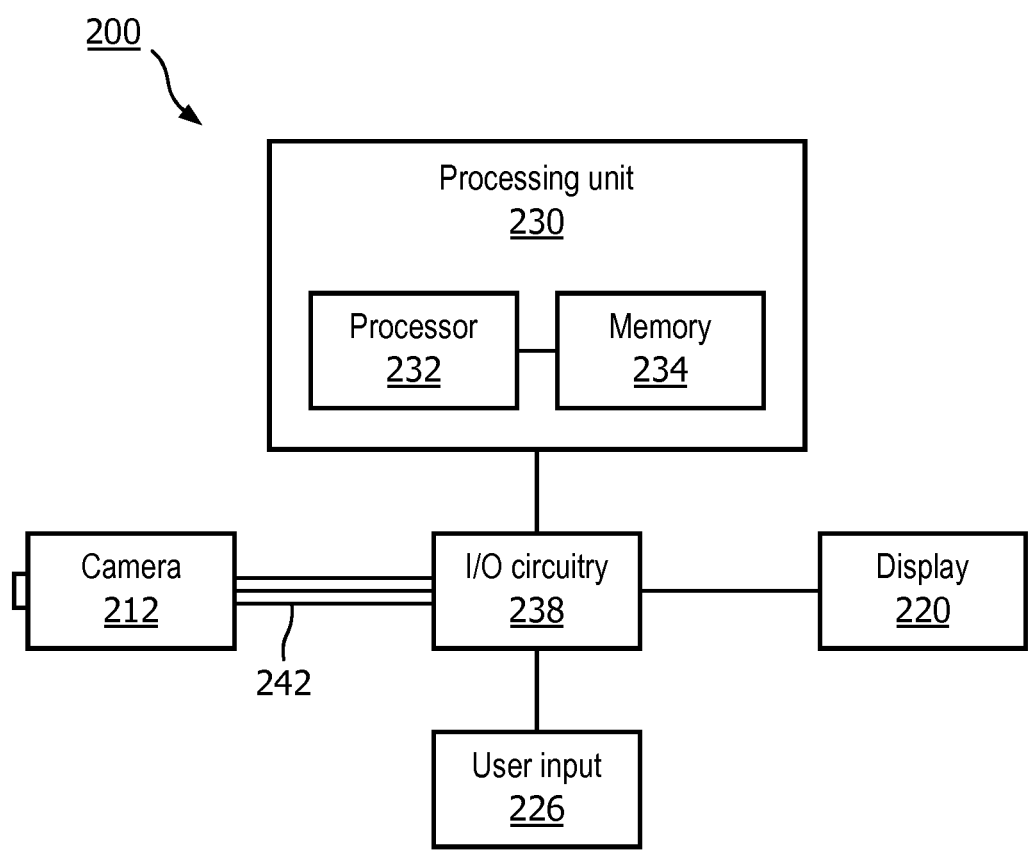
FIG. 2 is a simplified schematic block diagram showing a vasculature imaging system for imaging vasculature in a region of interest, according to a representative embodiment.

FIG. 2 is a simplified schematic block diagram showing a vasculature imaging system for imaging vasculature in a region of interest, according to a representative embodiment.

Referring to FIG. 2, imaging system 200 is provided for detecting abnormal tissue within a subject using vascular features. The imaging system 200 includes a camera 212 attached to a distal end of an interventional instrument 242, such as an endoscope, catheter and/or an end-effector of a robot arm. In an embodiment, the camera 212 has color video acquisition capability, and may provide digital still images and/or video. The camera 212 is insertable within the subject in order to image a target portion (e.g., or ROI), to determine the associated vascularity. Analysis of the vascularity enables differentiation between normal tissue and abnormal tissue, such as a cancerous tumor, as discussed below. More particularly, the camera 212 provides vasculature signals, including color image data and/or motion data (when the camera 212 provides digital video signals), corresponding to multiple pixels.

The camera 212 may be a monocular camera to 2D images or a stereo camera to capture 3D images, without departing from the scope of the present teachings. A stereo camera or a pair of cameras, for example, may include multiple lenses or lens assemblies with a separate sensor for each lens that forms an image on a digital detector array (e.g., a charge-coupled device (CCD) imaging array, a complementary metal-oxide-semiconductor (CMOS) imaging array, or the like). The camera 212 may have color video capability, e.g., by having an imaging array with pixels sensitive to red, green and blue light (or another set of colors substantially spanning the visible spectrum). The camera 212 optionally may include other typical features, such as a built-in flash (not shown) and/or an ambient light sensor (not shown) for setting exposure times.

The imaging system 200 further includes a processing unit 230, a display 220, a user input 226, and input/output circuit 238. The processing unit 230 includes at least one processor 232 and at least one memory 234. The memory 234 is a non-transitory storage medium, such as Random Access Memory (RAM), Read Only Memory (ROM), a magnetic disk and/or a solid state memory, for example. The memory 234 includes instructions that, when executed by the processor 232, cause the processor 232 to receive and process the vasculature signals of images provided by the camera 212. Generally, the processing identifies pixels of the camera 212 indicative of abnormal vascularity in the target portion, the abnormal vascularity corresponding to abnormal tissue. The processing also includes creating vascular maps depicting the abnormal vascularity with improved contrast using various techniques, including frequency, signal characteristics and phase variability, discussed below, for example. The vascular maps may be overlaid on images of the target portion to assist the user in identifying and treating (e.g., removing, biopsying) the abnormal tissue. The processing unit 230 is shown as having a wired connection to the camera 212 via the interventional instrument 242 (and the I/O circuitry 238). However, it is understood that the processing unit 230 may be connected to the camera 212 via a wireless communication link or network, such as Wi-Fi or 4G, for example, without departing from the scope of present teachings.

The processed images and/or vascular maps may be displayed on the display 220 (e.g., an LCD display, an OLED display, and/or a touch sensitive screen). The user (e.g., surgeon) is able to control the display 220 via the user input 226 (e.g., a mouse, a keyboard, a trackball, and/or a touch sensitive screen). For example, the user may isolate portions of the image, zoom in and out, and the like. When the camera 212 provides video signals, the user may pause at various frames, and move forward and backward in the video stream, for example. In this way, the user may overlay the vascular map(s) on a selected image frame on the display 220. The user may also manually control positioning of the camera 212 and/or the interventional instrument 242 via the user input 226, as discussed further below.

In an embodiment, the user input 226 and the display 220 may be incorporated within an AR-HUD device. The AR-HUD device may include left-eye and right-eye displays as the display 220, but alternatively the display 220 may be a single large window that spans both eyes. In some examples, the camera 212 provides a "first person view" so as to align AR content with the actual view seen through the display(s) of the AR-HUD device. In some examples, the AR-HUD device can be configured as a helmet, a headband, glasses, goggles, or other suitable embodiment in order to be worn on the head of the user.

As mentioned above, vascular maps may be created in order to identify pixels from among the multiple pixels in the camera 212 indicative of abnormal vascularity. Two or more of any combination of the vascular maps may be combined to provide an aggregate vascular map with enhanced contrast of area(s) with abnormal vascularity. The vascular maps and/or the aggregate vascular map may be translated to a portion of the subject that includes abnormal tissue, such as a tumor. Once identified, the portion of the subject with the abnormal vascularity may be removed from the subject, or otherwise contained or eliminated through various treatments, such as radiation therapy, cryotherapy, and high intensity focused ultrasound (HIFU) therapy, for example.

In order to obtain the vascular maps, variations in signals corresponding to vasculature images provided by the camera 212 are amplified, e.g., by the processor 232. In an embodiment, the signal variations may be amplified using Eulerian video magnification algorithm, although other amplification techniques may be incorporated without departing from the scope of the present teachings. Accordingly, subtle signal variations in the still or video images provided by the camera 212, not easily detected from the raw video images, are enhanced.

Figure 3:
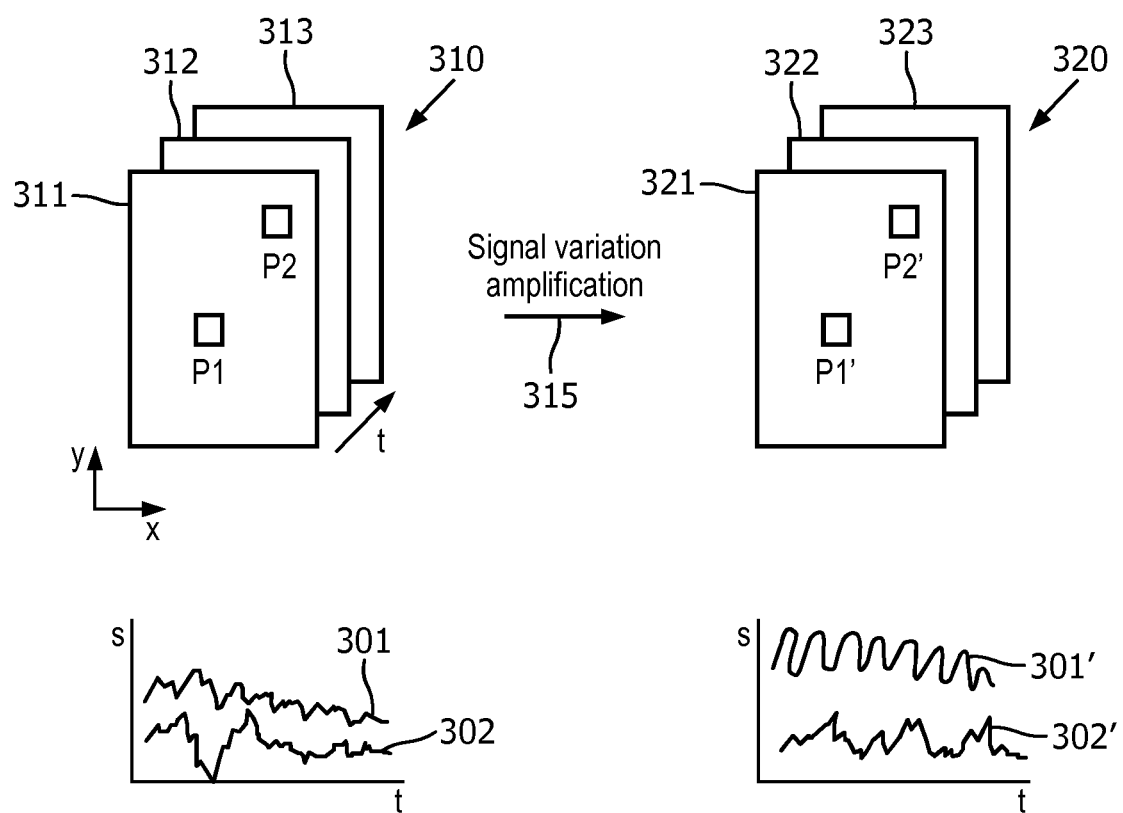
FIG. 3 is a simplified schematic drawing showing amplified images and corresponding signals captured in multiple image frames, according to a representative embodiment.

FIG. 3 is a simplified schematic drawing showing amplified images and corresponding signals captured in multiple image frames, according to a representative embodiment.

Referring to FIG. 3, image stream 310 includes a set of image frames 311, 312 and 313 provided over time by the camera 212, as indicated by the t-axis. The image frames 311, 312 and 313 contain images of a target portion of the subject. Representative pixels P1 and P2 of a pixel array are shown in image frame 311 (and are likewise included in subsequently acquired image frames 312 and 313, although they are blocked from view by the image frame 311 in the orientation shown in FIG. 3). Below the image stream 310 is a graph showing signals 301 and 302 as a function of time, the signals 301 and 302 corresponding to the pixels P1 and P2, respectively.

With respect to the image frames 311, 312 and 313, subtle signal variations over time of the representative pixels P1 and P2 are amplified. In various embodiments, the amplified signals include amplifying of motion variations, e.g., using known Eulerian Motion Magnification indicated by arrow 315. See, e.g., Wu et al., "Eulerian Video Magnification for Revealing Subtle Changes in the World," ACM Transactions on Graphics vol. 31 no. 4 (Proc. SIGGRAPH, 2012). For example, the variation of pixel values over time is amplified in a spatially-multiscale manner to effectively provide motion magnification. Use of Eulerian Motion Magnification may rely on exaggerating motion by amplifying temporal color changes at fixed positions, for example.

The resulting image stream 320 includes images with the amplified variations, which may be referred to as "amplified images" for the sake of discussion. The image stream 320 includes signals from pixels with magnified or amplified motion variations, which may be referred to as "amplified pixels" for the sake of discussion, enabling easier detection. Generally, the variations in signals 301 and 302 (along with signals corresponding to other pixels in the pixel array) are amplified over a desired time period, resulting in signals 301' and 302', discussed below. The image stream 320 includes a set of amplified image frames 321, 322 and 323 (with corresponding amplified pixels) corresponding to the image frames 311, 312 and 313, respectively. The pixels P1' and P2', corresponding to the pixels P1 and P2, respectively, are included in the amplified image frames 321, 322 and 323 (although shown only in amplified image frame 321). It is understood that signals with amplified variations corresponding to other pixels of the pixel array are also provided, although the present description is focused on the representative pixels P1' and P2' for ease of explanation.

Below the image stream 320 is a graph showing the signals 301' and 302' as a function of time, where the signals 301' and 302' corresponding to the pixels P1' and P2', respectively. The traces and/or waveforms of the signals 301' and 302' show subtle changes not apparent in the signals 301 and 302 due to the signal variation amplification. It is thus apparent, in this example, that the signal 301' is essentially sinusoidal with smooth transitions in the expected frequency range, consistent with an arterial waveform (e.g. pulsatile or corresponding to the cardiac cycle or pulse rate). Thus, a portion of the image provided by pixel P1' is consistent with normal physiology with respect to blood flow through normal tissue (normal vascularity). In comparison, the signal 302' is not sinusoidal, but rather has an irregular pattern. Thus, a portion of the image provided by pixel P2' does not have a waveform or frequency consistent with normal physiology regarding. In other words, pixel P2' may be identified as being indicative of abnormal vascularity (consistent with blood flow through abnormal tissue and/or tumors), based on at least frequency and shape. In other words, the portion of the image shown by pixel P2' corresponds to abnormal tissue, such as, for example, a cancerous tumor.

Figure 4:
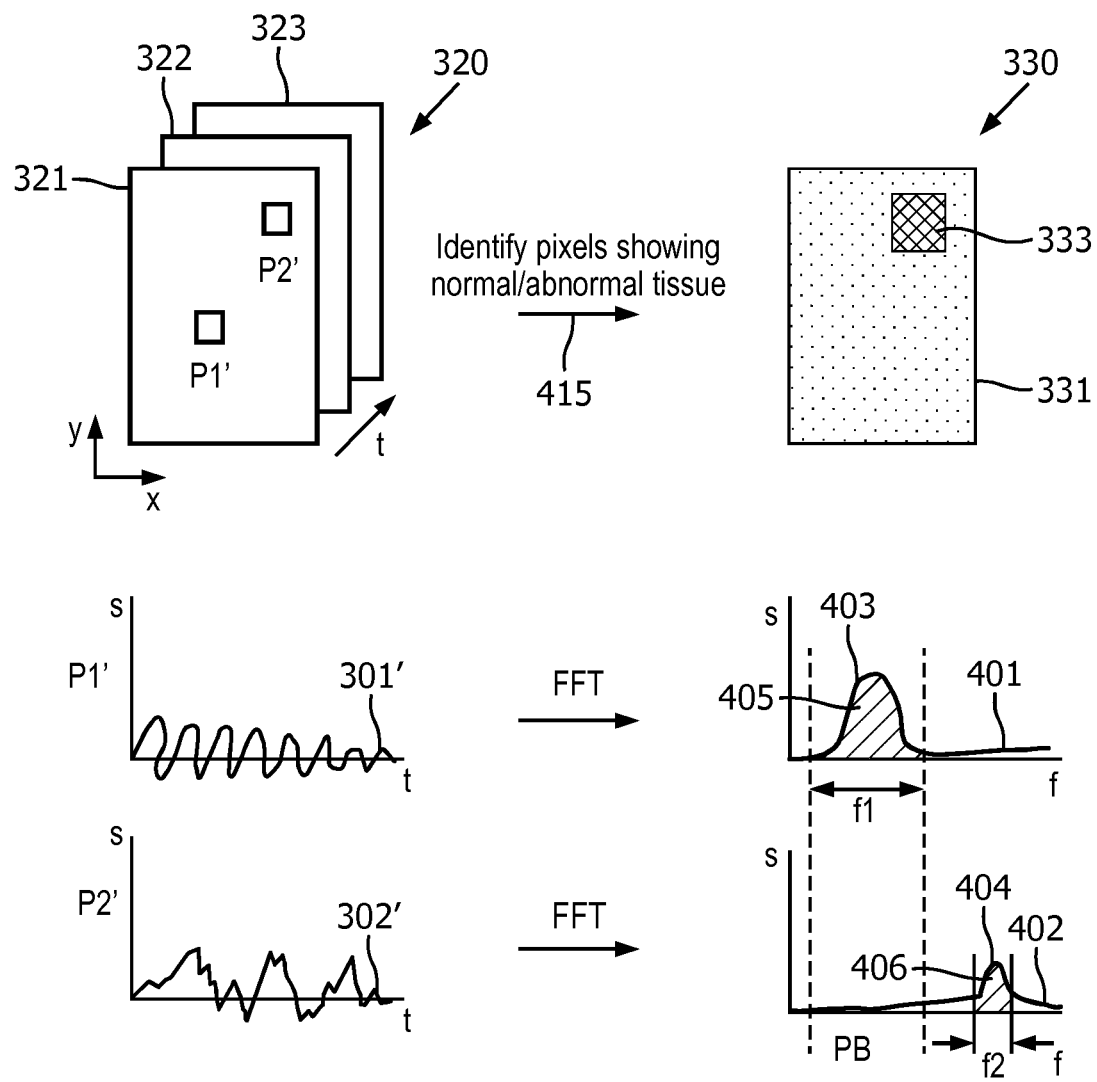
FIG. 4 is a simplified schematic drawing showing frequency and signal strength using amplified images and corresponding signals captured in multiple image frames, according to a representative embodiment.

FIG. 4 is a simplified schematic drawing showing frequency and signal strength using amplified images and corresponding signals captured in multiple image frames, according to a representative embodiment.

Referring to FIG. 4, the image stream 320 includes the amplified image frames 321, 322 and 323 provided over time, and amplified pixels P1' and P2' included in the amplified image frames 321, 322 and 323, as discussed above. Below the image stream 320 is a graph showing signal 301' and another graph showing signal 302' as a function of time, the signals 301' and 302' corresponding to the pixels P1' and P2', respectively, as discussed with reference to FIG. 3. As shown in FIG. 4, a fast Fourier transform (FFT) is performed on each of the signals 301' and 302' to decompose the signals 301' and 302' into their respective frequency components. That is, performing a FFT on the signal 301' in the time domain provides frequency spectrum 401 in the frequency domain corresponding to the magnified pixel P1', and performing a FFT on the signal 302' in the time domain provides the frequency spectrum 402 in the frequency domain corresponding to the magnified pixel P2'. The frequency spectrum 401 includes a peak 403 within a first frequency range f1, and the frequency spectrum 402 includes a peak 404 within a second frequency range f2 higher than the first frequency range f1. The frequency of the horizontal axis (frequency) may be scaled as beats per minute, for example.

By identifying the peaks 403 and 404, it can be determined whether the components of the peaks (e.g., that apex and the area beneath each of the peaks 403 and 404 in the frequency ranges f1 and f2) are within the physiological feasible passband PW, which is the frequency passband that corresponds to a credible range of pulse rates for the subject. For example, a credible range may have a lower limit of 40 beats/minute and an upper limit of 200 beats/minute, although the credible range maybe vary between other lowest and/or other highest values that are realistic, without departing from the scope of the present teachings. Decomposing the signals into their respective frequency components and identifying the largest peak components may be accomplished by windowing in the frequency domain, followed by a slope inversion and a local peak search, for example.

Referring to FIG. 4, it is apparent that peak 403 is within the physiological feasible passband PW, and thus indicates that the portion of the image provided by pixel P1' is consistent with normal physiology with respect to blood flow through normal tissue (normal vascularity). The peak 404 is outside the physiological feasible passband PW (i.e., at a higher frequency), and thus indicates that the portion of the image provided by pixel P2' is consistent with abnormal physiology with respect to blood flow through abnormal tissue (abnormal vascularity).

FFTs may be performed on signals corresponding to all pixels of the image stream 320, or on at least an adequate sampling of pixels of the image stream 320, to determine whether the peaks in the resulting frequency spectra are within the physiological feasible passband PW, as discussed above with reference to pixels P1' and P2'. A frequency map 330 can then be derived based on this information, indicated by arrow 415. A normal portion 331 of the frequency map 330 includes locations of the pixels (including pixel P1') having frequency spectra with peaks within the physiological feasible passband PW. An abnormal portion 333 of the frequency map 330 includes locations of the pixels (including pixel P2') having frequency spectra with peaks outside the physiological feasible passband PW. As can be seen, the abnormal portion 333 covers the vicinity in which the magnified pixel P2' is located. The larger the abnormal portion 333, the more pixels it encompasses, indicating a larger area of abnormal vascularity, and thus a larger area of abnormal tissue. Of course, a resulting frequency map could display multiple portions that indicate abnormal vascularity, without departing from the scope of the present teachings.

In addition, the characteristics of the signals 301' and 302', and variations of the underlying frequency components, can be extracted by performing FFT on each of the signals 301' and 302', and finding area under the curve (AUC) and/or full width half max (FWHM) of the strongest frequency components in the resulting frequency spectra 401 and 402, respectively. Referring again to FIG. 4, the AUC 405 of the peak 403 is larger than the AUC 406 of the peak 404. The larger AUC 405 indicates a more normal vascularity associated with the pixel P1' than the pixel P2'. In order to determine whether the peak 403 actually indicates the presence of abnormal tissue using the AUC 405, the AUC 405 may be compared to a predetermined AUC threshold value, since a pixel may have a smaller corresponding AUC than another pixel in the array without necessarily indicating the presence of abnormal tissue. The range of "normal" AUCs may be determined empirically, for example.

A signal characteristics map 430 (shown in FIG. 6) may be derived from the AUCs of the frequency domain signals corresponding to the pixels, including pixels P1' and P2'. A normal portion 431 of the signal characteristics map 430 includes locations of the pixels (including pixel P1') having AUC within the normal range (e.g., below the predetermined AUC threshold value), and an abnormal portion 433 of the signal characteristics map 430 includes locations of the pixels (including pixel P2') having AUC outside the normal range (e.g., above the predetermined AUC threshold value). Essentially the same type of map can be derived using FWHM values. As can be seen, the abnormal portion 433 covers the vicinity in which the abnormal tissue located, and the normal portion 431 covers the vicinity in which normal tissue is located. The signal characteristics map 430 may be similar in appearance to the frequency map 330 since they are derived from the same FFTs of the signals 301' and 302'. Of course, a signal characteristics map could display multiple portions that indicate abnormal vascularity, without departing from the scope of the present teachings.

Notably, in the example shown in FIG. 4, the pixel P2' can already be identified as indicating abnormal tissue since its peak 403 is outside the physiological feasible passband PW, as discussed above. Thus, determining the characteristics of the corresponding signal 302' to determine whether the pixel P2' shows normal or abnormal tissue may be used as an alternative method. Or, both methods may be used and combined for redundant confirmation (creating an aggregate enhanced contrast map, as discussed below with reference to FIG. 6, for example).

Also, higher level features may be extracted from the signals 301' and 302' indicative of signal shape and pulsatility using a long-term short-term memory (LTSM) network or a recurrent neural network (RNN) to understand the respective shapes the signals in the time domain. Each signal value would be treated like a word. The LTSM network and the RNN takes into account time sequence information. LTSM networks may be particularly useful to make associations between farther separated time points in the signals 301' and 302'. As stated above, the signal 301' is essentially sinusoidal with smooth transitions in the expected frequency range, consistent with normal tissue, while the signal 302' is not sinusoidal, but rather has an irregular pattern, consistent with abnormal tissue.

Figure 5:
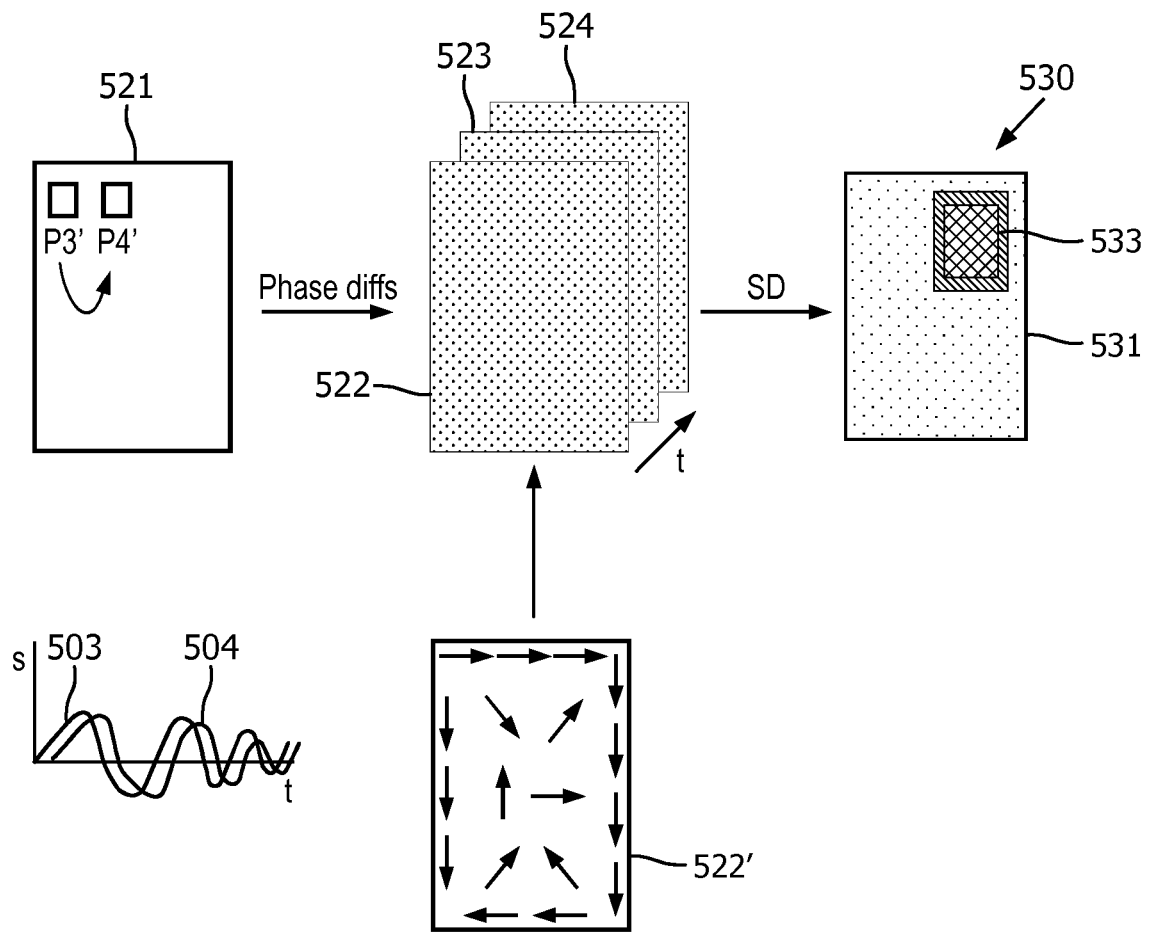
FIG. 5 is a simplified schematic drawing showing phase shifts between pixels within an amplified image and corresponding phase signals captured in one or more image frames, according to a representative embodiment.

FIG. 5 is a simplified schematic drawing showing phase shifts between neighboring pixels within an amplified image and corresponding phase signals captured in one or more image frames, according to a representative embodiment. Phase shifts (or phase differences) between neighboring pixels among the multiple pixels of the amplified image steam(s) are identified and compared with one another to determine spatial phase variability. The phase shifts of the main sinusoidal signal between neighboring pixels are used to understand the directionality and organization of flow in a vascular system.

Referring to FIG. 5, amplified image frame 521 includes representative amplified pixels P3' and P4', which are neighboring (e.g., adjacent) pixels in the pixel array. The amplified image frame 521 may be obtained by amplifying variations in signals corresponding to vasculature images provided by the camera 212, as discussed above with regard to the amplified image frame 321, for example. However, amplified pixels P1' and P2' are not shown in FIG. 5 for purposes of explanation since they are not neighboring pixels. Below the amplified image frame 521 is a graph showing signals 503 and 504 as a function of time, where the signals 503 and 504 correspond to the pixels P3' and P4', respectively. The signals 503 and 504 are offset from one another, indicating phase shift.

This phase shift information is collected to provide multiple phase maps corresponding to an amplified image frame, as shown by representative phase maps 522, 523 and 524 in FIG. 5, which correspond to the amplified image frame 521, for example. That is, the series of images in an image frame can be compressed into multiple phase maps, so that multiple amplified image frames can be provided for a period of time. Phase map 522' corresponds to the representative phase map 522, and depicts illustrative arrows or vectors indicating phase shifts between various neighboring pixels, e.g., pixels P3' and P4', and which can estimate direction of flow.

The mean and standard deviation of the phase shifts are determined for the phase maps 522, 523 and 524. Generally, the standard deviations corresponding to pixels showing areas with irregular vascular flow (indicating abnormal tissue) are higher than standard deviations corresponding to pixels showing areas with regular vascular flow. A phase variability map 530 can then be derived based on the phase maps 522, 523 and 524. A normal portion 531 of the phase variability map 530 identifies locations of the pixels with phase shifts having low standard deviations, and an abnormal portion 533 of the phase variability map 530 identifies locations of the pixels with phase shifts having high standard deviations. The standard deviations may be compared to a predetermined threshold value, identifying the value at which the standard deviation begins to indicate irregular vascular flow. The range of "abnormal" and/or "normal" standard deviations may be determined empirically, for example. Of course, a resulting standard deviation map could display multiple portions that indicate abnormal vascularity, without departing from the scope of the present teachings.

More particularly, multiple phase maps (e.g., three or four), such as the phase maps 522, 523 and 525, are taken for different periods of time. The mean and the standard deviation at each pixel of the phase maps 522, 523 and 525 are determined, and the information from the phase maps 522, 523 and 524 are combined into the phase variability map 530. Thus, information may be obtained about the extent of irregularity of flow (if any), the directionality of flow, and organization of the vasculature.

Figure 6:
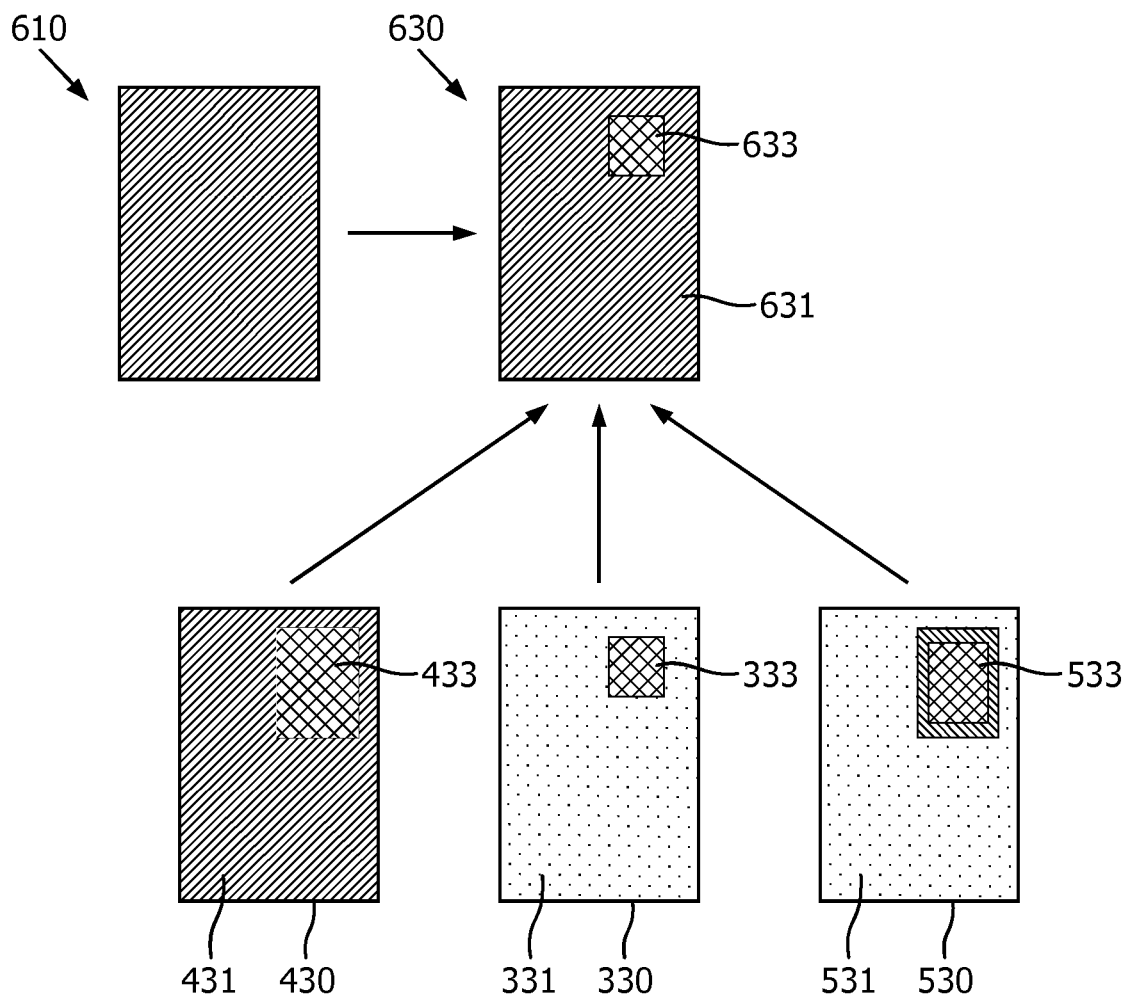
FIG. 6 is a simplified schematic drawing showing vascular maps obtained by the techniques described with reference to FIGS. 3-5, combined to provide an aggregate vascular map with enhanced contrast, according to a representative embodiment.

FIG. 6 is a simplified schematic drawing showing vascular maps obtained by the techniques described with reference to FIGS. 3-5, combined to provide an aggregate vascular map with enhanced contrast, according to a representative embodiment.

Referring to FIG. 6, map 610 is an original vascular map of a target portion with effectively no contrast. That is, the camera images do not provide sufficient contrast, pixel-to-pixel, between areas of normal vascularity (normal tissue) and abnormal vascularity (abnormal tissue or tumors, for example). In comparison, aggregate vascular map 630 shows a sharp contrast between a normal portion 631 and an abnormal portion 633 of a target portion or ROI.

In the depicted embodiment, the aggregate vascular map 630 is a combination three other vascular maps obtained through different techniques, improving the contrast over any of the other vascular maps viewed on its own. The three other vascular maps include the frequency map 330, the signal characteristics map 430 and the phase variability map 530, discussed above. The vascular features can be displayed as the frequency map 330, the signal characteristics map 430 and/or the phase variability map 530, and as the aggregate vascular map 630 (with the increased contrast in the abnormal tissue or tumor region).

An embodiment includes training a simple logistic regression (or other classifiers could be used) per pixel or per pixel cluster classifier to determine the best combination of the frequency map 330, the signal characteristics map 430 and/or the phase variability map 530, to improve contrast of malignant lesions. An embodiment includes providing different weights to pixels or portions of abnormal vascularity, depending on whether the abnormality appears in one, two or all three of the other vascular maps. The highest weights are assigned to pixels or portions of the images that show abnormality in all three of the other vascular maps, and the lowest weights are assigned to pixels or portions of the images that show abnormality in only one of the other vascular maps. The aggregate vascular map 630 may then be created using the weights. Of course, other techniques for combining vascular maps into the aggregate vascular map 630 may be incorporated without departing from the scope of the present teachings. Also, the aggregate vascular map 630 may combine fewer than all three other vascular maps, without departing from the scope of the present teachings. Thus, in various embodiments, the aggregate vascular map 630 may be based on at least one of frequency, signal characteristics and spatial phase variability of at least some of the vasculature signals corresponding to the plurality of pixels in the pixel array, respectively.

As described above, the camera may provide images during an interventional procedure. The camera therefore may be mounted to a distal end of an interventional instrument or tool, such as an endoscope or catheter, and/or mounted to a robot arm, to direct the camera to the target portion or ROI within the subject.

Figure 7A:
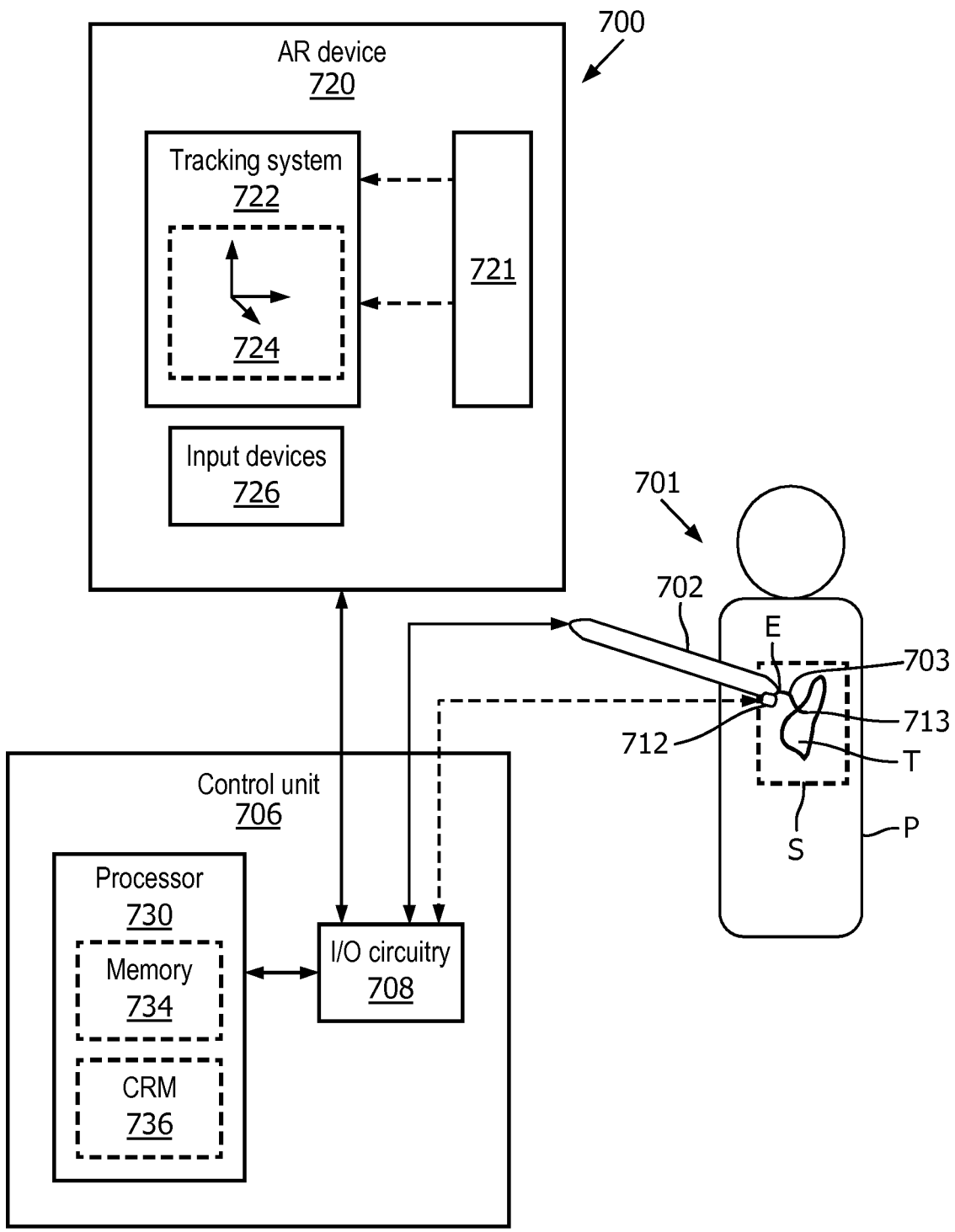
FIG. 7A is a schematic block diagram showing a surgical robot system, in accordance with an illustrative embodiment of the present invention.

FIG. 7A is a schematic block diagram showing an example of a surgical robot system that may be used for obtaining images, enabling performance of interventional procedure(s), in accordance with representative embodiments of the present disclosure. FIG. 7A depicts surgical robot system 700, which may be utilized for medical procedures, typically involving manipulation of surgical instruments and other tools operable by a robot at a surgical site located within a patient's body. Such medical procedures include, but are not limited to, minimally invasive cardiac surgery, abdominal surgery (laparoscopy) (e.g., prostatectomy or cholecystectomy), and natural orifice translumenal endoscopic surgery, for example.

Referring to FIG. 7A, the surgical robot system 700 includes at least one robot 701, a control unit 706, and an augmented reality (AR) device 720. The robot 701 is configured to operate one or more end-effectors to be positioned at a surgical site S within a subject P, including at least one camera 712 (or similar image acquisition device) configured to acquire live images at the surgical site S and at least one instrument 713, such as a surgical tool for performing an internal surgical procedure. Internal surgical procedures may include minimally invasive surgeries or natural orifice surgeries, for instance, involving a target portion T within the surgical site S, examples of which are mentioned above.

The AR device 720 is configured to display the live images acquired by the camera 712 on an AR display unit 721 to be viewed by the user, and to detect tracking data using a AR tracking system 722 that captures the user's movements (responsive to the displayed images) via one or more motion sensing circuits, indicated by representative motion sensor 724. For example, as discussed further below, the AR device 720 may be a head mounted heads-up display (HUD) device (AR-HUD device) including a head piece worn by the user that includes the display unit 721 and the motion sensor 724. The display unit 721 may be a single display or it may be divided into two eye displays (not shown), corresponding to the eyes of the user. The two eye displays enable three-dimensional viewing when the camera 712 is stereoscopic or pseudo three-dimensional viewing when the camera 712 is monocular, but the two eye displays are configured to partially overlap. The motion sensor 724 may be multiple accelerometers, for example, for detecting motion of the user's head around three axes, such that the tracking data comprises head-tracking data corresponding to head movements of the user. Alternatively, the motion sensor 724 may include backward facing camera(s) for detecting movement of the user's eyes, such that the tracking data comprises eye-tracking data corresponding to eye movements of the user.

The AR device 720 also may include one or more input devices (e.g. user interfaces), indicated by input device 726, for receiving instructions from the user. The input device 726 as used herein is an interface which allows the user to interact with the AR device 720, as well as the surgical robot system 700. The input device 726 may include one or more of a touch screen, keyboard, mouse, trackball, touchpad, or voice command interface, for example. In the present embodiment, the user may use the input device 726 to enter specific commands, such as sending an acknowledgment signal to processor 730 to confirm a selected target portion T as determined by the processor 730, or to send an activation signal to the AR tracking system 722 and/or the processor 730 to activate one of a head-tracking mode that includes the detection of the head motion by the HUD device or an eye-tracking mode that includes the detection of the eye movements by the HUD device. In alternative embodiments, the input device 726 may be outside the AR device 720. For example, the input device 726 may be integrated into the control unit 706 or may be a separate unit configured to communicate with both the AR device 720 and the processor 730 via the I/O circuitry 708.

The control unit 706 is configured to control and otherwise coordinate overall operations of the surgical robot system 700. The control unit 706 includes input/output (I/O) circuitry 708 and a processor 730. The processor 730 includes associated memory 734 for enabling the processing and computer readable medium (CRM) 736. The processor 730 and the memory 734/the CRM 736 may be substantially similar to the processing unit 230 of the imaging system 200 discussed above with reference to FIG. 2. The processor 730 is generally configured to receive the acquired live images from the camera 712 via the I/O circuitry 708, and to process and store the acquired live images, e.g., in the memory 734 and/or the CRM 736, so that the processor 730 is able to build a database, such as an electronic medical record (EMR) database and/or a picture archiving and communication system (PACS) database, essentially visually mapping interior portions of the subject P traversed by the camera 712. This database may be used subsequently to determine a path to the target portion T, once the target portion T has been selected, as discussed below. The processor 730 transmits the acquired live images to the AR device 720 via the I/O circuitry 708 for display on the display unit 721. In alternative configurations, the acquired live images may be transmitted to the AR device 720 from the I/O circuitry 708 upon receiving the acquired live images by the I/O circuitry 708, without any imaging processing performed by the processor 730.

The processor 730 is further configured to receive tracking data to determine by the AR tracking system 722 from the AR device 720 via the I/O circuitry 708, and to process the determined tracking data to select a target (e.g., the target portion T) at the surgical site S within the subject P. The processor 730 is further configured to determine a path for the one or more end-effectors of the robot 701, e.g., including the illustrative camera 712 and instrument 713, to reach the selected target portion T based upon the acquired live images and the processed determined tracking data. The processor 730 transmits robot control signals to the robot 701 via the I/O circuitry 708 to move the one or more end-effectors to the selected target portion T along the determined path.

Accordingly, the I/O circuitry 708 receives the acquired live images from the camera 712, and provides the acquired live images to the processor 730 and/or to the AR device 720 (either directly or forwarded from the processor 730 after image processing) for display on the display unit 721. The I/O circuitry 708 also receives the input data (including tracking data) from the AR device 720, which it provides to the processor 730, and sends robot control signals determined by the processor 730 in response to the tracking data to the robot 701.

The robot 701 may have a rigid proximal portion 702 (e.g., a robot arm or a portion of a robot arm) to be positioned at an entry point E in the body of the subject P, and a flexible distal portion 703 to be positioned at a surgical site S within the subject P. The robot 701 is broadly defined herein as any robotic device structurally configured with motorized control of one or more joints and two or more corresponding links for maneuvering the flexible distal portion 703 as desired for the particular robotic procedure. The flexible distal portion 703 may include one or more end-effectors, including the camera 712 and the instrument 713. The instrument 713 may be a gripper or a tool holder, a laparoscopic instrument, laparoscope, a tool for screw placement, e.g., in spinal fusion surgery, a needle for biopsy or therapy, an ultrasonic transducer for tissue or tumor imaging and ablation, or other surgical or interventional tool, for example. For purely exploratory interventional procedures, the flexible distal portion 703 may include just the camera 712.

In practice, as would be appreciated by those skilled in the art, the robot 701 may have a minimum of three (3) degrees-of-freedom, and beneficially six (6) or more degrees-of-freedom. The robot 701 may have a remote center of motion (RCM) mechanism with two intersecting motor axes. Also, the robot 701 may have associated therewith a light projection apparatus (not shown). An example of a steerable or dexterous surgical robotic device which may be incorporated is a seven-degree of freedom universal wrist, such as described by Sanchez, U.S. Pat. No. 7,121,781 (Oct. 17, 2006), which is hereby incorporated by reference. The universal wrist includes multiple joints and jaws at the distal portion, and the drive system at the proximal portion. The device can further be positioned using a robotic positioner and computer controller. The robotic positioning allows for tracking of the device motion with respect to anatomy. An end-effector may be coupled to the wrist, which provides two separate degrees of freedom about the same pivot point. The end-effector can be moved and actuated by pins, allowing for a compact minimally invasive medical instrument.

Although a single robot 701 for operating a single rigid proximal portion 702 and a single corresponding distal portion 703 is depicted in FIG. 7A, it is understood that multiple robots with corresponding multiple rigid proximal portions and/or multiple rigid distal portions may be incorporated without departing from the scope of the present teachings. That is, the robot 701 may include multiple robotic arms (not shown) controlling different end-effectors in the surgical site S with multiple cameras 712. For example, one robotic arm may include a forward-looking camera, such as the camera 712 for providing the live images of the surgical site S, while another robotic arm may include the instrument 713, as well as additional instrument (s).

The camera 712 defines part of an imaging system with control unit 706 of the surgical robot system 700, which is substantially similar to imaging system 200 discussed above with reference to FIG. 2. The camera 712 may include one or more of any type of camera having a forward optical view or an oblique optical view, and may be capable of acquiring a sequence of two-dimensional digital video frames at a predefined frame rate (e.g., 30 frames per second) and capable of providing each digital video frame to the control unit 706 via the input/output circuitry 708. In particular, the camera 712 may be a forward-looking camera positioned and oriented such that within its field of view it can acquire live images of the surgical site S and the target portion T (e.g. an organ) from the flexible distal portion 703 of the robot 701. In an embodiment, the rigid proximal portion 702 may be an endoscope-like device controlled by the robot 701, where the single rigid proximal portion 702 includes multiple channels, one of which enables control of and/or communication with the camera 712 and at least one other of which enables entry and control of the instrument 713 or other end-effectors. In alternative embodiments, the camera 712 is mounted to the flexible distal portion 703 corresponding to the rigid proximal portion 702, while other end-effectors may be in flexible distal portions corresponding to other rigid proximal portions (not shown), all of which are controlled via the robot 701. In yet another embodiment, the camera 712 is mounted to the flexible distal portion of a separate endoscope, not part of the robot 701, but rather under control of a separate endoscope controller (operating in conjunction with the robot 701), as discussed below with reference to FIG. 7B. Also, the camera 712 may be a stereoscopic camera or stereoscopic endoscope that provides images that can be perceived in three dimensions. An example of a stereoscopic endoscope is described by Breidenthal et al., U.S. Pat. No. 6,139,490 (Oct. 31, 2000), which is hereby incorporated by reference. Alternatively, the camera 712 may be monocular and the display unit 721 is divided into two eye displays corresponding to the user's eyes, in which case, the monocular image is split in two overlapping halves and presented on each of the two eye displays separately to create a pseudo-stereo view.

An external medical imagery device may also be included. The medical imagery device may be configured to acquire a live image or live images of the flexible distal portion 703 of the surgical robot 701 and the target portion T at the surgical site S, providing a more comprehensive overview. Such a medical imagery device may include a C-arm (not shown) at least partially surrounding a portion of the subject P. C-arms have radiographic capabilities, and may be used for fluoroscopic imaging during surgical procedures, as is known to those skilled in the art. An example of a C-arm, implementing an X-ray system, is described by Popovic, U.S. Pat. No. 9,095,252 (Aug. 4, 2015), which is hereby incorporated by reference.

Figure 7B:
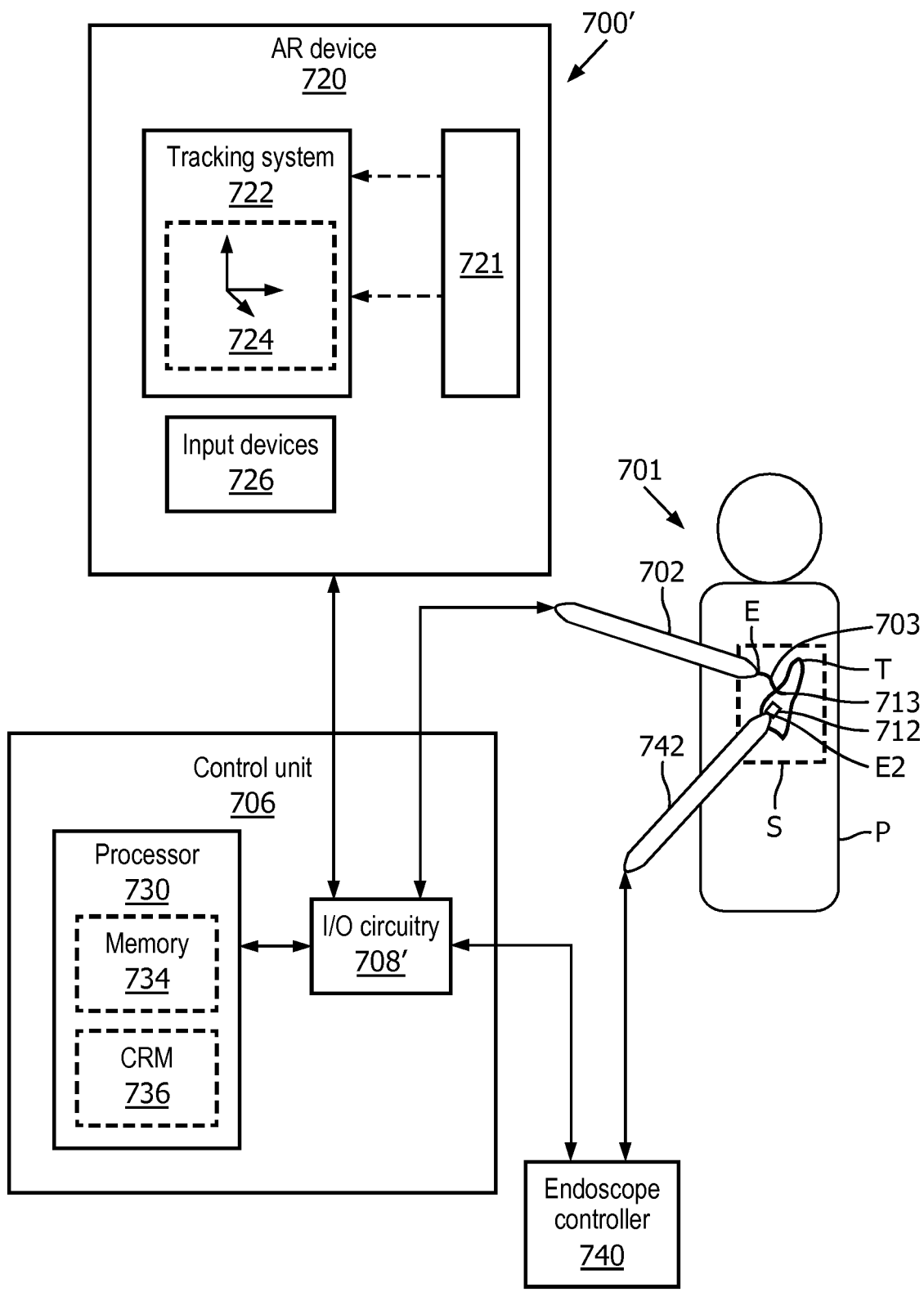
FIG. 7B is a schematic block diagram showing a surgical robot system, in accordance with an illustrative embodiment of the present invention.

FIG. 7B is a schematic block diagram showing a surgical robot system, in accordance with a representative embodiment, including a separate imaging endoscope and corresponding endoscope controller. FIG. 7B depicts surgical robot system 700', which may be utilized for medical procedures, typically involving manipulation of surgical instruments and other tools operable by a robot at a surgical site located within a subject's body, as discussed above.

Referring to FIG. 7B, in the depicted embodiment, the surgical robot system 700' is similar to the surgical robot system 700 in that it includes at least one robot 701, a control unit 706, and a AR device 720. The robot 701 is configured to operate one or more end-effectors to be positioned at a surgical site S within a subject P, including at least one instrument 713, such has a surgical tool for performing an internal surgical procedure.

In addition, the surgical robot system 700' includes endoscope controller 740 configured to control endoscope 742, which is separate from the robot 701. The endoscope 742 includes the camera 712 mounted to the distal end. The endoscope 742 and camera 712 are configured to acquire live images within the body at the surgical site S. The AR device 720 is configured to display the live images acquired by the camera 712, as discussed above. In various embodiments, the endoscope 742 may include a rigid or flexible tube, a light delivery system to illuminate the organ or object under inspection (e.g. the light source is normally outside the body and the light is typically directed via an optical fiber system), a lens system transmitting the image from the objective lens to the viewer, typically a relay lens system in the case of rigid endoscopes or a bundle of fiber optics in the case of a fiberscope. Also contemplated are videoscopes, with no eyepiece, in which a camera transmits images to a screen for image capture. Also, in various embodiments, the camera 712 may be stereoscopic, for example, where image data enables display of apparent three-dimensional images, e.g., on the AR display unit 721.

In the depicted example, the robot 701 has a rigid proximal portion 702 to be positioned at a first entry point E1 in the body of the subject P, and a flexible distal portion 703 to be positioned at a surgical site S within the subject P. The endoscope 742 includes a sheath to be positioned at a second entry point E2 in the body of the subject P. The endoscope 742 may include multiple channels, one of which provides the image acquisition, and at least one other of which enables entry and control of another instrument, such as a medical instrument or manipulator, and/or a light source for illuminating the surgical site S, to be controlled by the endoscope controller 740.

The control unit 706 is configured to control and otherwise coordinate overall operations of the surgical robot system 700', including control and coordination of the robot 701 and the endoscope 742. The control unit 706 includes I/O circuitry 708', which differs from the I/O circuitry 708 in that it has an additional interface(s) for communicating with the endoscope controller 740. Thus, the processor 730 is generally configured to receive the acquired live images from the camera 712 via the endoscope controller 740 and the I/O circuitry 708', and to process and store the acquired live images, e.g., in the memory 734 and/or the CRM 736, so that the processor 730 is able to build a database essentially visually mapping interior portions of the subject P traversed by the endoscope 742. This database may be used subsequently to determine a path to the target portion T, once the target portion T has been selected, as discussed below. The processor 730 transmits the acquired live images to the AR device 720 via the I/O circuitry 708' for display on the display unit 721. In alternative configurations, the acquired live images may be transmitted to the AR device 720 from the I/O circuitry 708' upon receiving the acquired live images by the I/O circuitry 708' from the endoscope controller 740, without any imaging processing performed by the processor 730.

The processor 730 is further configured to receive tracking data to determine by the AR tracking system 722 from the AR device 720 via the I/O circuitry 708', and to process the determined tracking data to select a target (e.g., the target portion T) at the surgical site S within the subject P. The processor 730 is further configured to determine a path for the one or more end-effectors of the robot 701, e.g., including the illustrative instrument 713, to reach the selected target portion T based upon the acquired live images and the processed determined tracking data. The processor 730 transmits robot control signals to the robot 701 via the I/O circuitry 708' to move the one or more end-effectors to the selected target portion T along the determined path.

Accordingly, the I/O circuitry 708' receives the acquired live images from the camera 712 via the endoscope 742 and the endoscope controller 740, and provides the acquired live images to the processor 730 and/or to the AR device 720 (either directly or forwarded from the processor 730 after image processing) for display on the display unit 721. The I/O circuitry 708' also receives the input data (including tracking data) from the AR device 720, which it provides to the processor 730, and sends robot control signals determined by the processor 730 in response to the tracking data to the robot 701.

Referring to the AR device 720 (shown in FIGS. 7A and 7B), the display unit 721 includes one or more displays that may be co-located near the user. For example, when the AR device 720 is implemented as a HUD device, the display unit 721 may be attached to the front of a head piece, directly in front of eyes of the user, like goggles. The display unit 721 is configured to display live images of the surgical site S, as discussed above, and the user moves his or her head and/or eyes observing the live images displayed on the display unit 721 and tracking a target for selection, thus simulating actual surgical procedures in which the surgeon moves his or her head and/or eyes to observer the surgical site and perform the procedure. When the camera 712 provides stereoscopic images, the live images displayed on the display unit 721 may appear to be three-dimensional. In an embodiment, the display unit 721 may also display preoperative images. Thus, the images from the at least one camera 712 are captured and displayed in the HUD device.

The HUD device may be referred to as an augmented-reality heads-up display (AR-HUD) device with one or more AR-HUD displays. An illustrative design employs left-eye and right-eye displays, but alternatively the display can be a single large window that spans both eyes. In some examples, the AR-HUD device can be configured as a helmet, a headband, glasses, goggles, or other suitable embodiment in order to be worn on the head of the user.

The processor 730 is able to identify or select the target portion T by processing the tracking data to determine the angle of the user's head in relation to the display unit 721 (and the live images displayed thereon), where the head angle indicates the region or point of the live image, which constitutes the target portion T within the surgical site S, at which the user is looking. Once the user is satisfied with the position of the target portion T in the surgical field S on the display unit 721, an acknowledgement signal may be sent to the processor 730 in the control unit 706 (e.g., via a foot pedal, a push button or a voice command). The processor 730 may assign (or address) coordinates in two or three dimensions corresponding to the selected target portion T. Knowing the location of the entry point E in the body of the subject P and the coordinates of the selected target portion T, together with the database of acquired live images from the camera 712, the processor 130 is able to determine a path (or vector(s)) for the at least one instrument 713 operable by the robot 701 to reach the selected target portion T. An example of determining such a path for a robotically controlled instrument to reach a target in a surgical site of a patient is provided by Popovic et al., U.S. Pat. No. 8,934,003 (Jan. 13, 2015), which is hereby incorporated by reference. The processor 730 is then able to transmit robot control signals to the robot 701 causing the robot 701 to guide a distal end of the at least one instrument 713 to the target portion T via the determined path. That is, the control unit 706 issues commands to robot 701 to move to the position of the selected target portion T. The requited motion of each joint of the robot 701 is implemented by the processor 730 using methods known in art. For example, the robot 701 may utilize visual serving methods known in art.

Referring again to FIGS. 7A and 7B, the control unit 706 may be broadly defined herein as any controller which is structurally configured to provide one or more control commands to control the acquisition and processing of images (e.g., live, exploratory, preoperative) from the camera 712 at the surgical site S, and the target portion T, and utilize tracking information related to selection of the target portion T from the AR device 720 to determine a path to the target portion T and to further control the flexible distal portion 703. Generally, the I/O circuitry 708 controls communication among elements and devices external to the control unit 706. The I/O circuitry 708 acts as an interface including necessary logic to interpret input and output signals or data to/from the processor 730, the AR device 720 and the robot 701. The I/O circuitry 708 may include a first input configured to receive the acquired live images from the camera 712, and a first output configured to provide the acquired live images to at least one of the processor 730 and the AR device 720 ultimately for display. The I/O circuitry 708 may further include a second input configured to receive determined input data, including tracking data, from the AR device 720, a second output configured to provide the determined input data to the processor 730, which processes the input data to identify and select the target portion T in response, and a third output configured to provide robot control signals to the robot 701.

The processor 730 may perform the described functions and operations using a combination of hardware, software and firmware. The processor 730 is configured to process medical imagery (e.g. from the camera 712 or an external medical imagery device) related to the flexible distal portion 703 of the surgical robot 701 at the surgical site S to register the flexible distal portion 703 with corresponding anatomy at the surgical site S. The processor 730 may be configured to process additional positional tracking information of the rigid proximal portion 702 of the surgical robot 701 from a position tracking system (not shown) to determine motion of the rigid proximal portion 702. The position tracking system, which is separate from the tracking system 722, may be one or more of an optical tracking system, mechanical tracking system, and electromagnetic tracking system, as would be appreciated by those skilled in the art. A sensor or tag (e.g. light emitting diodes (LEDs), passive markers, reflective markers, etc.) may be included at the rigid proximal portion 702 of the surgical robot 701 to cooperate with the position tracking system. In an embodiment, a position compensation mode may be provided, according to which the processor 730 is configured to generate motion compensation signals for the flexible distal portion 703 of the surgical robot 701 based upon the determined positions and motion of the rigid proximal portion 702.

In practice, the discussed control processes may be implemented by modules that are embodied by any combination of hardware, software and/or firmware installed on any platform (e.g., a general computer, application specific integrated circuit (ASIC), field programmable gate array (FPGA), etc.). Furthermore, processes may be performed by the processor 730 of control unit 706.

As used in the specification and appended claims, the terms "a", "an" and "the" include both singular and plural referents, unless the context clearly dictates otherwise. Thus, for example, "a device" includes one device and plural devices. Also, it is to be understood that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B).

As used herein, the statement that two or more parts or components are "coupled" shall mean that the parts are joined or operate together either directly or indirectly, i.e., through one or more intermediate parts or components, so long as a link occurs.

Directional terms/phrases and relative terms/phrases may be used to describe the various elements' relationships to one another, as illustrated in the accompanying drawings. These terms/phrases are intended to encompass different orientations of the device and/or elements in addition to the orientation depicted in the drawings.

A "computer-readable storage medium" as used herein encompasses any tangible storage medium which may store instructions which are executable by a processor of a computing device. The computer-readable storage medium may be referred to as a non-transitory computer-readable storage medium, to distinguish from transitory media such as transitory propagating signals. The computer-readable storage medium may also be referred to as a tangible computer-readable medium.

In some embodiments, a memory and/or computer-readable storage medium may also be able to store data which is able to be accessed by the processor of the computing device. Examples of memory and computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to "computer storage" or "storage" should be interpreted as possibly including multiple storage devices or components.

For instance, the storage may include multiple storage devices within the same computer system or computing device. The storage may also include multiple storages distributed amongst multiple computer systems or computing devices.

A "processor" as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have instructions performed by multiple processors that may be within the same computing device or which may even be distributed across multiple computing devices.

A "user interface" or "user input device" as used herein is an interface which allows a user or operator to interact with a computer or computer system. A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the user's control or manipulation. The display of data or information on a display or a graphical user interface is an example of providing information to an operator. The receiving of data through a touch screen, keyboard, mouse, trackball, touchpad, pointing stick, graphics tablet, joystick, and headset (e.g., AR-HUD) are all examples of user interface components which enable the receiving of information or data from a user.

A "display" or "display device" or "display unit" as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

While various embodiments have been illustrated and described in detail in the drawings and foregoing description, such illustration and description are to be considered illustrative or exemplary and not restrictive; the invention is not limited to the disclosed embodiments.

The invention claimed is:

1. A imaging system comprising:
    a camera, having color video acquisition capability, mounted to a distal end of an interventional instrument insertable within an object, the camera providing a plurality of image frames for imaging vasculature of the object, each image frame comprising a plurality of pixels providing corresponding signals, respectively;
    a display; and
    a processor programmed to:
        receive the signals;
        amplify variations in at least one of color and motion of the signals corresponding to the plurality of pixels to provide amplified signals;
        determine at least one of spatial phase variability, frequency and signal characteristics of at least some of the amplified signals corresponding to the plurality of pixels, respectively;
        identify pixels of the plurality of pixels indicative of abnormal vascularity based on the at least one of spatial phase variability, frequency and signal characteristics of the at least some of the amplified signals;
        create a vascular map corresponding to each of the at least one of spatial phase variability, frequency and signal characteristics of the at least some of the amplified signals using the identified pixels, each vascularity map including a portion of the object having the abnormal vascularity; and
        operate the display to display each vascularity map.

2. The imaging system of claim 1 wherein the processor is further programmed to create an aggregate vascular map comprising a combination of at least two of the vascular maps corresponding to each of the at least one of spatial phase variability, frequency and signal characteristics of the at least some of the amplified signals.

3. The imaging system of claim 2, wherein the aggregate vascular map provides a sharper contrast between the portion of the object having the abnormal vascularity and another portion of the object having normal vascularity than a contrast provided by any one of the vascular maps corresponding to each of the at least one of spatial phase variability, frequency and signal characteristics of the at least some of the amplified signals.

4. The imaging system of claim 1 wherein the variations in at least one of color and motion of the signals are amplified using Eulerian video magnification.

5. The imaging system of claim 1, wherein the processor is programmed to identify the pixels indicative of abnormal vascularity based on spatial phase variability by:
    determining phase shifts between adjacent pixels of the plurality of pixels, respectively;
    providing phase maps corresponding to amplified image frames, each amplified image frame comprising the plurality of pixels;
    determining standard deviations of the phase shifts between the adjacent pixels for the phase maps; and
    identifying the pixels in the phase maps having standard deviations higher than a threshold standard deviation, corresponding to normal vascularity, as being indicative of abnormal vascularity.

6. The imaging system of claim 1, wherein the processor is programmed to identify the pixels indicative of abnormal vascularity based on frequency includes by:
    determining frequency components of the amplified signals corresponding to the plurality of pixels, respectively; and
    identifying the pixels having corresponding frequency components outside a physiological feasible passband as being indicative of abnormal vascularity.

7. The imaging system of claim 6, wherein the physiological feasible passband corresponds to a credible range of pulse rates of the object.

8. The imaging system of claim 6, wherein the processor is programmed to identify the pixels having corresponding frequency components outside the physiological feasible passband by:

performing Fourier transforms on the amplified signals to provide corresponding frequency spectra;

identifying largest peak components in the frequency spectra; and determining whether the largest peak components are outside the physiological feasible passband, respectively.

9. The imaging system of claim 1, wherein the processor is programmed to identify the pixels indicative of abnormal vascularity based on signal characteristics by:

performing Fourier transforms on the amplified signals to provide corresponding to frequency spectra;

identifying largest peak components in the frequency spectra;

determining areas under curve (AUCs) or full width at half maximums (FWHMs) of the largest peak components, respectively; and identifying the pixels having corresponding AUCs or FWHMs less than a threshold AUC or FWHM corresponding to normal vascularity, as being indicative of abnormal vascularity.

10. The imaging system of claim 1, wherein the interventional instrument comprises an endoscope.

11. The imaging system of claim 2, wherein the aggregate vascular map is created based on a combination of all of the vascular maps corresponding to each of spatial phase variability, frequency and signal characteristics of the at least some of the amplified signals.

12. The imaging system of claim 2, the display is incorporated within an augmented reality heads-up display (AR-HUD) device for displaying at least one of the vascular maps or the combination of at least two of the vascular maps, the AR-HUD device comprising a head piece worn by a user.

13. A method for identifying abnormal vascularity, indicating abnormal tissue within a subject, using images from a camera having color video acquisition capability and mounted to a distal end of an interventional instrument insertable within the subject, the method comprising:

receiving signals corresponding to a plurality of pixels in each of a plurality of image frames provided by the camera of a target portion in the subject for imaging vasculature of the target portion;

amplifying variations in at least one of color and motion of the signals corresponding to the plurality of pixels in each of the plurality of image frames to provide amplified signals, respectively;

determining at least one of spatial phase variability, frequency and signal characteristics of at least some of the amplified signals corresponding to the plurality of pixels, respectively;

identifying pixels of the plurality of pixels in each of the plurality of image frames indicative of abnormal vascularity based on the at least one of spatial phase variability, frequency and signal characteristics of the at least some of the amplified signals;

creating a vascular map corresponding to each of the at least one of spatial phase variability, frequency and signal characteristics of the at least some of the amplified signals using the identified pixels, each vascularity map including a portion of the subject having the abnormal vascularity; and displaying each vascularity map.

14. The method of claim 13, further comprising:

combining at least two of the vascular maps corresponding to each of the at least one of spatial phase variability, frequency and signal characteristics of the at least some of the amplified signals to create an aggregate vascular map; and displaying the aggregate vascular map.

15. A computer readable medium containing software, executable by a computer processor, for identifying abnormal vascularity, indicating abnormal tissue within a subject, using images from a camera having color video acquisition capability and mounted to a distal end of an interventional instrument insertable within the subject, the computer readable medium comprising:

receiving code for receiving signals corresponding to a plurality of pixels in each of a plurality of image frames provided by the camera via the interventional instrument of a target portion in the subject for imaging vasculature of the target portion;

amplifying code for amplifying variations in at least motion of the signals corresponding to the plurality of pixels in each of the plurality of image frames to provide amplified signals, respectively;

determining code for determining at least one of spatial phase variability, frequency and signal characteristics of at least some of the amplified signals corresponding to the plurality of pixels, respectively;

identifying code for identifying pixels of the plurality of pixels in each of the plurality of image frames indicative of abnormal vascularity based on the at least one of spatial phase variability, frequency and signal characteristics of the at least some of the amplified signals;

creating code for creating a vascular map corresponding to each of the at least one of spatial phase variability, frequency and signal characteristics of the at least some of the amplified signals using the identified pixels, each vascularity map including a portion of the subject having the abnormal vascularity;

combining code for providing an aggregate vascular map by combining at least two of the vascular maps corresponding to each of the at least one of spatial phase variability, frequency and signal characteristics of the at least some of the amplified signals; and displaying code for causing the aggregate vascular map to be displayed on a display, the displayed aggregate vascular map indicating the portion of the subject having the abnormal vascularity by enhanced contrast with portions of the subject having normal vascularity.

* * * * *